US007300799B2

United States Patent
Ijdo et al.

(10) Patent No.: US 7,300,799 B2
(45) Date of Patent: Nov. 27, 2007

(54) METHOD TO ASSESS ORGANOCLAY EXFOLIATION AND ORIENTATION IN ORGANOCLAY/POLYMER COMPOSITES

(75) Inventors: Wouter Ijdo, Trenton, NJ (US); Steven Kemnetz, Trenton, NJ (US); Wilbur Mardis, Holland, PA (US); Daphne Benderly, Metuchen, NJ (US)

(73) Assignee: Elementis Specialties, Inc., Highstown, NJ (US)

( * ) Notice: Subject to any disclaimer, the term of this patent is extended or adjusted under 35 U.S.C. 154(b) by 281 days.

(21) Appl. No.: 11/165,948

(22) Filed: Jun. 24, 2005

(65) Prior Publication Data

US 2006/0292697 A1    Dec. 28, 2006

(51) Int. Cl.
  *G01N 30/00* (2006.01)
(52) U.S. Cl. .................. 436/164; 422/82.05; 436/174; 436/171
(58) Field of Classification Search .............. 436/164, 436/172, 171; 422/82.05
See application file for complete search history.

(56) References Cited

U.S. PATENT DOCUMENTS 5,554,670 A    9/1996    Giannelis et al.

OTHER PUBLICATIONS

Organoclay Complexes and Interactions (Shmuel Yariv et al.) published by Marcel Dekker Inc., New York (2002), pp. 345-348.
International Search Report for PCT/US2006/24061 dated Jan. 25, 2007.

*Primary Examiner*—Jill Warden
*Assistant Examiner*—Samuel P Siefke
(74) *Attorney, Agent, or Firm*—Morgan, Lewis & Bockius, LLP (57) ABSTRACT

A method for determining degree of organoclay delamination and degree of layer alignment in a polymer organoclay nanocomposite comprising one or more infrared light spectral measurements selected from the group consisting of (A) Si—O absorption bandwidth, (B) Si—O absorption band intensity, (C) Si—O absorption band area, and (D) Si—O absorption anisotropy.

9 Claims, 6 Drawing Sheets

METHOD TO ASSESS ORGANOCLAY EXFOLIATION AND ORIENTATION IN ORGANOCLAY/POLYMER COMPOSITES

BACKGROUND OF THE INVENTION

This invention relates to polymer clay nanocomposites, and more particularly to methods of measuring properties of such composites including devices especially designed to practice such methods.

Polymer clay nanocomposites are formed when nano-sized clay additives are dispersed into a plastic. The dispersion of nanoscopic particles in polymers can provide materials properties that can not easily be achieved by the incorporation of conventional macroscopic fillers. Nanocomposites based on organically modified smectite clays (organoclays) have received significant attention over the last decade but unmodified clays have also been incorporated in plastics. Examples of important applications for these clay and organoclay nanocomposites are in the area of flame retardancy, barrier enhancement, composite strength, and improvements in thermal stability. Elementis Specialties, Inc., assignee hereof, is the world's largest manufacturer of organoclays and is a recognized leader in research and development relating to this field.

Hydrous phyllosilicate clays are particularly useful for the preparation of polymer organoclay nanocomposites. These hydrous phyllosilicate clays are layered, platy materials where the individual clay layers are aggregated into discrete particles. Useful phyllosilicate clays include smectite clays such as: montmorillonite; bentonite; hectorite; saponite; stevensite; and beidellite, for example. Other useful phyllosilicate clays are vermiculite and certain micas. Hectorite, montmorillonite and bentonite are particularly useful. Both naturally occurring- or synthetic-clays, particularly synthetic hectorite, may be used in the preparation of polymer clay nanocomposites. When the word clay is used hereafter, it includes both natural and synthetic clays.

Clay layers are hydrophilic because they carry a net negative charge that is neutralized by hydrophilic metal ions that are positioned between the surfaces of the clay layers. Organic surface treatment is often necessary to produce modified clays called organoclays that have improved compatibility with organic systems. An organoclay is formed when the hydrophilic metal ions are exchanged with organic cations. Such organoclays are easily prepared and are readily available as discussed hereafter.

Polymer organoclay nanocomposite benefits are realized when one or more organoclays is delaminated to the "nano" state in a polymer. It is generally accepted that, ideally, all organoclay particles are dispersed towards individual layers in a delamination process to form a polymer composite containing discrete nano-sized layers. This "delamination of layers" is at times also referred to as "exfoliation of layers" and both terms can be used interchangeably. However, complete dispersion of these organoclays towards their nano-sized state is not easily accomplished. Incomplete organoclay dispersion and delamination leaves microsized particles in the plastic which may alter the materials properties of the resulting nanocomposite. The degree of organoclay dispersion in plastics is extremely difficult to control and such inability can result in unpredictable materials properties. Clay nano-dispersion repeatability and reproducibility has been a long-felt need in the field of clay nanocomposites. If such repeatability and reproducibility could be achieved, polymer organoclay nanocomposites would likely become much more successful in the marketplace.

Currently there is no facile analytical method available to quantify the degree of organoclay delamination in plastics. Transmission electron microscopy (TEM), X-ray Diffraction (XRD) and Thermogravimetric analysis (TGA) are widely used to characterize polymer organoclay nanocomposites, but none of these methods can effectively quantify the degree of organoclay delamination; they merely provide a rough idea about the clay dispersion state. Furthermore, certain applications benefit when the delaminated layers are arranged in an aligned state. Nanocomposites that are targeted to deliver enhanced barrier properties preferably have exfoliated and aligned clay platelets. Analysis of clay layer alignment alone is not meaningful for such composites as the clay platelets could be aligned while still being stacked in particles or agglomerates. Layer alignment is only meaningful for such composite materials when interpreted in conjunction with the degree of layer delamination. Furthermore, measurement of degree of delamination alone is not meaningful for these nanocomposite as the application depends on the presence of delaminated and aligned clay layers.

A general introduction to assess materials orientation via the aid of polarized vibrational spectroscopy is discussed by Everall in, "Using polarized vibrational spectroscopy to characterize molecular orientation in polymers: An introduction—a tutorial," *The Internet Journal of Vibrational Spectroscopy,* 3(2), 1998, where the author disclosed using vibrational spectroscopy to quantify crystalline and amorphous phase orientation in polyethylene.

For background on clays and spectroscopy, also see Schaefer, et al., "Extent of dispersion of an organo-clay complex in oil. An infrared method," *NLGI Spokesman,* 34, 418 (1971), which discloses that the silicon-oxygen (Si—O) bond infrared (IR) absorption bandwidth reduces when organoclay is dispersed in mineral oil to produce grease.

Note that the clay layer orientation has been determined for a Nylon 6-clay nanocomposite film using a combination of infrared and TEM analysis, as disclosed by Loo, et al., in "Investigation Of Polymer And Nanoclay Orientation Distribution In Nylon6/Montmorillonite Nanocomposite," *Polymer,* 45, 5933 (2004).

A quick and easy to use analytical method that is able to measure the degree of organoclay delamination and layer alignment in a polymer-organoclay nanocomposite is very desirable. The above mentioned techniques have not been shown to address this issue. With the aid of an analytical method that can assess clay layer dispersion and orientation, polymer organoclay nanocomposite producers could guarantee the quality and consistency of their polymer composite products.

SUMMARY OF THE INVENTION

In one aspect the invention comprises a method for determining degree of organoclay delamination and layer alignment in a polymer organoclay nanocomposite comprising selected regions from one or more infrared light absorption spectra selected from the group consisting of (A) silicon-oxygen (Si—O) absorption bandwidth, (B) Si—O absorption band intensity, (C) Si—O absorption band area, and (D) Si—O absorption band anisotropy.

DETAILED DESCRIPTION OF THE INVENTION

The method of the invention is useful for determining degree of organoclay delamination and degree of layer alignment in a polymer organoclay nanocomposite. Selected regions within one or more infrared light absorption spectra can be used according to the invention, i.e., (A) Si—O absorption bandwidth, (B) Si—O absorption band intensity, (C) Si—O absorption band area, and (D) Si—O absorption anisotropy. The method of the invention makes use of characteristic absorption bands in the infrared region of both clay and polymer.

Clays and organoclays have very characteristic silicon-oxygen (Si—O) stretching absorption bands around the 1000-1100 $cm^{-1}$ region. Clays have two types of Si—O bonds, each of which absorb at a specific frequency within this region; those Si—O bonds that are oriented roughly within the plane of the clay layer (in-plane Si—O bonds), and those bonds that are oriented perpendicular (normal) to the layer plane (out-of-plane Si—O bonds). The infrared absorption bands of these bonds can be used to monitor organoclay dispersion.

The optical properties (position, relative intensity, shape and bandwidth of absorption bands) of a material in the infrared region are dependent on the size and shape of the (agglomerated) particles, and on the nature of the matrix in which the material is in embedded. Infrared light absorption is related to the dielectric constant of the absorbing medium, which should have some value between that of the embedding matrix and the particles, where the latter depends on the state of particle aggregation in the matrix. Therefore, bandwidth broadening is ascribed to agglomeration of clay layers. Conversely, the absorption bands narrow as the clay platelets become increasingly delaminated and absorption bands that initially overlap may become better resolved. The Si—O stretching absorption bands do not resolve further, nor is a further reduction in absorption bandwidth observed, once all layers are completely isolated from other clay platelets. The method of the invention uses Si—O stretch infrared absorption bands to estimate the degree of clay layer delamination in plastics.

Vibrations in a molecular bond only give rise to infrared light absorption if the dipole moment of the bond changes during a vibration. The dipole moment is related to, but does not necessarily coincide with, the direction of the bond. The absorption intensity will be greatest when infrared light is polarized in the same direction as the oscillating dipole, but will diminish when the light is polarized at an angle towards the dipole. The absorption intensity depends on the square of the cosine of the angle between the absorbing dipole and the polarization direction of the infrared light beam. Thus, the silicate bonds in a composite sample where clay layers are aligned will absorb infrared light that is polarized in one direction with a different efficiency than light polarized in a different direction. This absorption anisotropy, or dichroism, is used to calculate a dichroic ratio, which can be correlated to the orientation of an absorbing bond. This approach may be used to estimate the average degree of clay layer alignment in clay containing systems. Alternatively, the dichroic values can also be used to compare different samples with each other to determine which of the samples is more, or less, aligned than others without assigning absolute values to the degree of orientation.

To obtain dichroic information for the Si—O bonds, one measures the absorption of infrared light that is polarized in one direction, and then one measures the absorption of light that is polarized in a different, typically perpendicular, direction. The absorption ratio is the dichroic ratio. If a sample has layer alignment, this dichroic ratio will depend on how the sample is oriented with respect to the incident beam. Hence, a dichroic ratio can be calculated for each sample tilt angle. If a sample has randomly oriented layers, then the dichroic ratio equals unity and is invariant with sample position.

Quantitative infrared absorption spectra may be obtained using a variety of devices and sample preparation procedures designed to obtain such information, including equipment that measures infrared absorption in either the transmission or reflectance modes.

A microcomposite is formed when organoclay particles (agglomerates) are dispersed into a plastic, but where delamination of layers fails to occur. Organoclay particles are present merely as stacks of layers. As set forth above, such a composite material will show a wide absorption band for the Si—O stretching bonds. Alternatively, when the clay is delaminated, as in an exfoliated nanocomposite, individual absorption bands will be seen for both the "in-plane" as well as "out-of-plane" Si—O bonds and these absorption bands will be relatively narrow in bandwidth. An intercalated nanocomposite is produced when polymer penetrates the organic interlayer to expand this interlayer distance by a fixed amount. Hence, the platelets in an intercalated nanocomposite will still be stacked in agglomerates, but there is more distance between the layers. The degree of layer interaction is thus reduced, and one can expect the two Si—O absorption bands to become more resolved from the absorption spectrum. This would be accompanied with a certain reduction in absorption bandwidth but less than is observed for an exfoliated organoclay nanocomposite.

The invention can be used to characterize nanocomposites with a wide variety of thermoplastic or thermoset plastic polymers, for example: polyolefins such as polyethylene, polypropylene, polybutylene and EVA; polystyrene; polyamides; urea-formaldehydes; epoxies; polyesters; polyvinyl chloride; thermoplastic polyurethanes, and; melamine-formaldehydes. Certain polymers such as polyethylene do not exhibit absorption bands in the region of 1000-1100 $cm^{-1}$, and therefore isol straightforward. However, polymers like polystyrene do show significant absorption in this region. In such instances, these absorption bands of the nanoclay-free plastic can be measured, and then subtracted from the polymer organoclay nanocomposite spectra by, e.g., Fourier Transform techniques. Polymer absorption bands close to the 1000-1100 $cm^{-1}$ region of interest can be used as a reference in the subtraction process.

The clays used in the nanocomposites to which the method of the invention is most useful are typically smectite clays, particularly bentonite and hectorite. Such clays are more fully defined in several patents owned by the assignee hereof including U.S. Pat. Nos. 6,521,690 and 6,380,295. These clays have long been made into organoclays by reaction with organic salts by well known techniques. See for example U.S. Pat. No. 5,336,647 granted to assignee herein, particularly columns 7 and 8. Hectorite clay is a so-called trioctahedral clay with layer charge mainly arising from substitution in the octahedral sites of the layer and, therefore, has only one major in-plane and one major out-of-plane Si—O stretching absorption band which can be readily identified. In contrast, bentonite clays are dioctahedral clays and also have considerable amounts of aluminum and/or iron substituted for silicon in the tetrahedral silicate sheet, and so multiple in-plane and out-of-plane absorption bands can be observed, which bands often do not resolve well from each other. Hence, it is far more difficult to deconvolute the bandwidth for a particular stretching frequency in bentonite clay when compared to hectorite clay. This becomes particularly important when polymer absorption bands coincide with the region of interest and need to be subtracted from the absorption pattern in order to isolate the clay contribution. Hectorite clay will allow for a more precise determination of the absorption bandwidth, and therefore this clay is more preferred when using this analytical technique. Other relatively pure clays, either from natural origin or synthetic, can also be used with relative ease. The method of the invention, however, can be used with less pure clays, such as bentonite.

The invention is illustrated by the following examples in which all parts and percentages are by weight unless otherwise indicated.

EXAMPLES

Example 1

Measurement of Organoclay Layer Exfoliation Using Si—O Infrared Absorption Bandwidth Polyethylene-hectorite organoclay (BENTONE® 108) composites were prepared using the solvent cast method. XRD analysis showed that a virtually completely exfoliated nanocomposite was obtained with the solvent cast preparation process when the organoclay was dispersed using a Cowles dissolver and polar activator (propylene carbonate, 30 percent by weight based on organoclay weight). An intercalated nanocomposite was obtained in the absence of polar activator. The solvent cast composites were obtained as fine powder-like materials. Next, homogeneous blends were prepared from these composites so that samples were obtained comprising various proportions of delaminated (exfoliated) and intercalated layers. In a similar approach, the exfoliated nanocomposite was blended with various amounts of BENTONE® 108 organoclay powder. All composite blends were processed so that homogeneous thin films could be prepared of constant thickness and formulated to contain 5 wt % organoclay.

Figure 1:
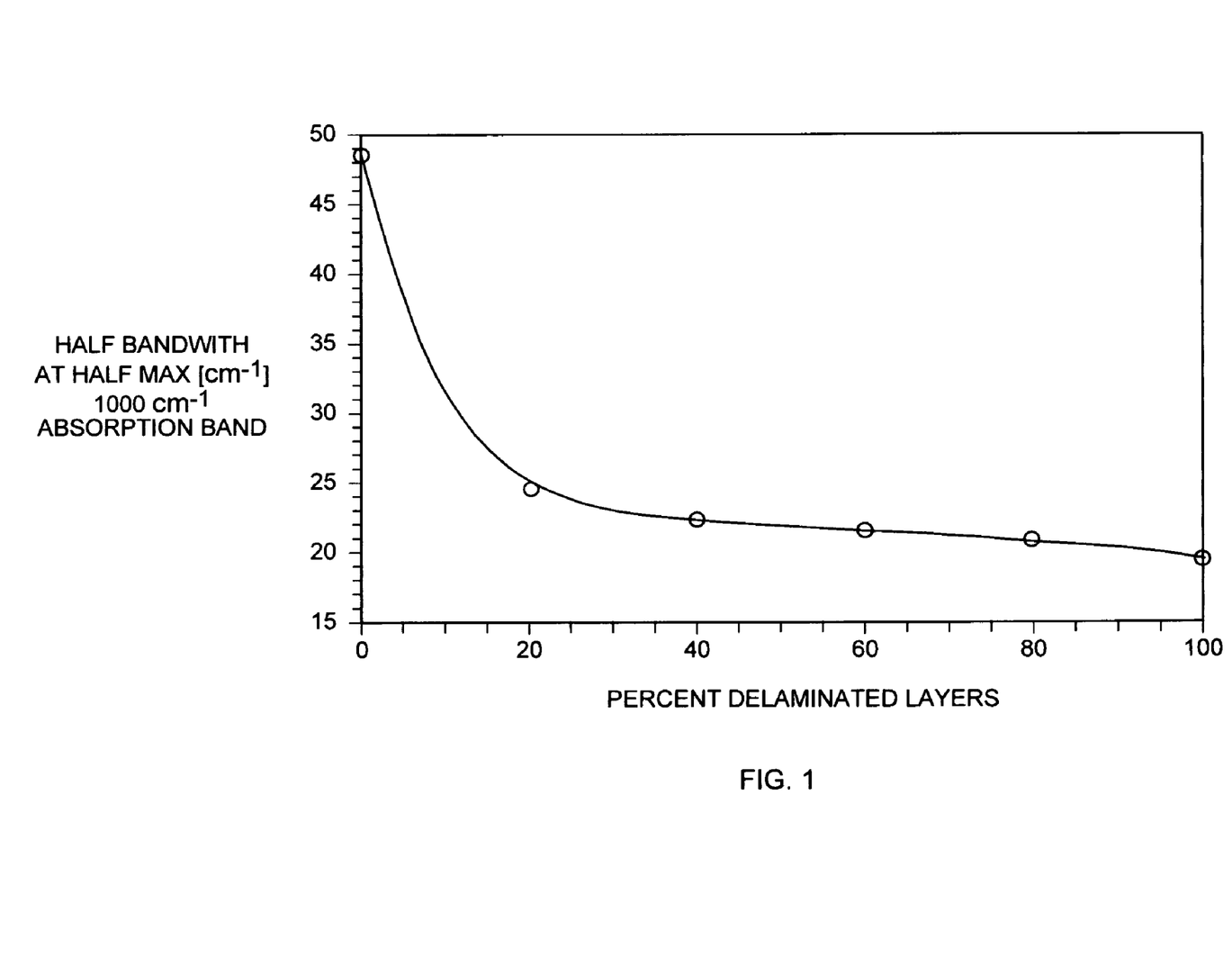
FIG. 1 is a graph showing the experimentally determined relationship between infrared absorption bandwidth and percent layer exfoliation of a hectorite-polyethylene composite that contains exfoliated organoclay layers and/or undispersed organoclay powder.
Figure 2:
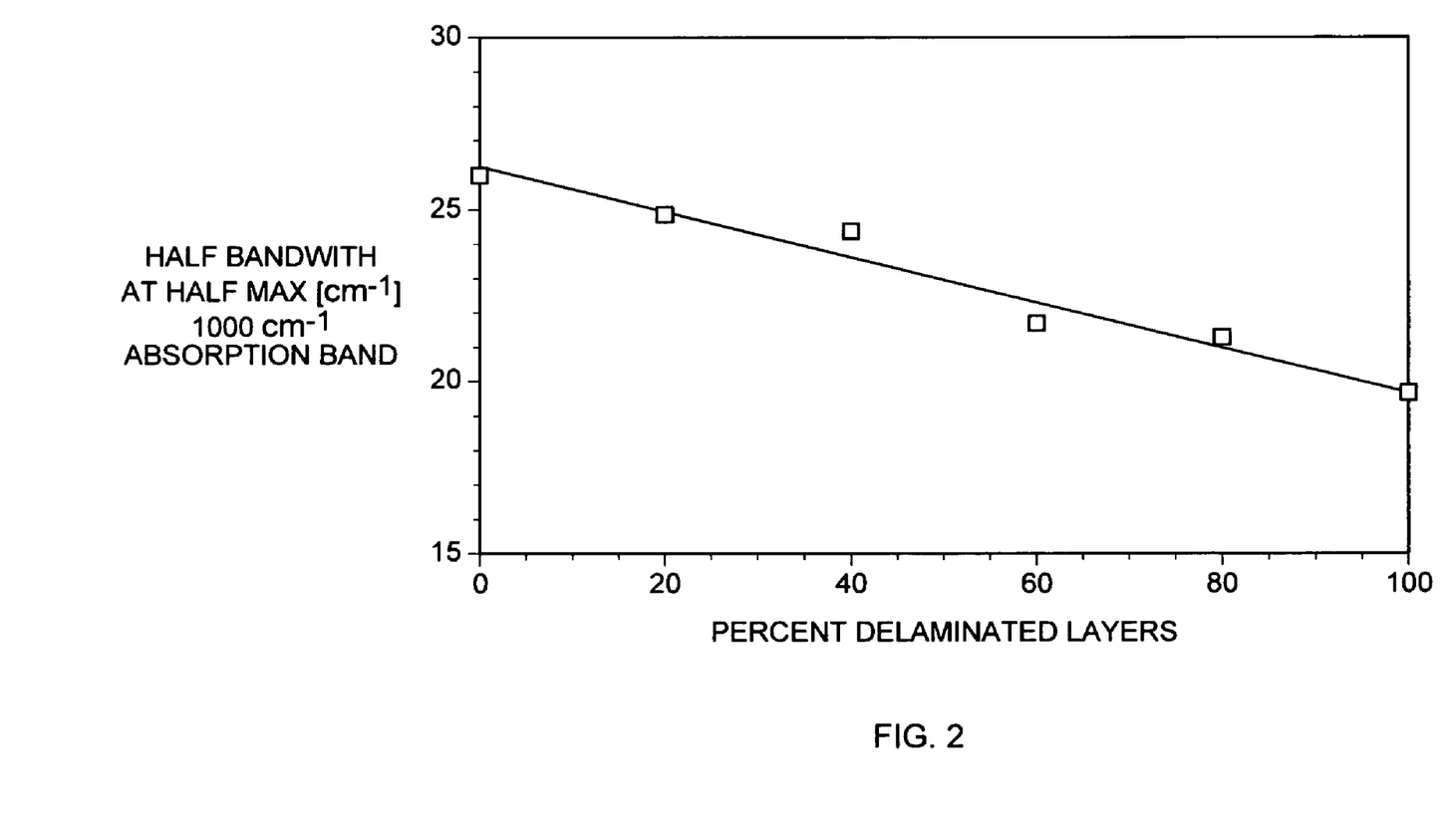
FIG. 2 is a graph showing the experimentally determined relationship between infrared absorption bandwidth and percent exfoliation of a hectorite-polyethylene composite comprised of exfoliated and intercalated organoclay layers.

The infrared light absorption spectra in transmission mode was recorded using unpolarized light and the variation of the Si—O bandwidth as function of degree of organoclay delamination is shown in FIGS. 1 and 2 for the absorption band around 1000 $cm^{-1}$ (this band corresponds to the in-plane Si—O bonds). It is clear that the Si—O absorption bandwidth decreases as the degree of exfoliation increases in the samples. One can estimate the degree of organoclay delamination by measuring the Si—O bandwidth using these figures as a calibration curve. Similar calibration curves may be constructed for other polymer composite systems.

Example 2

Figure 3:
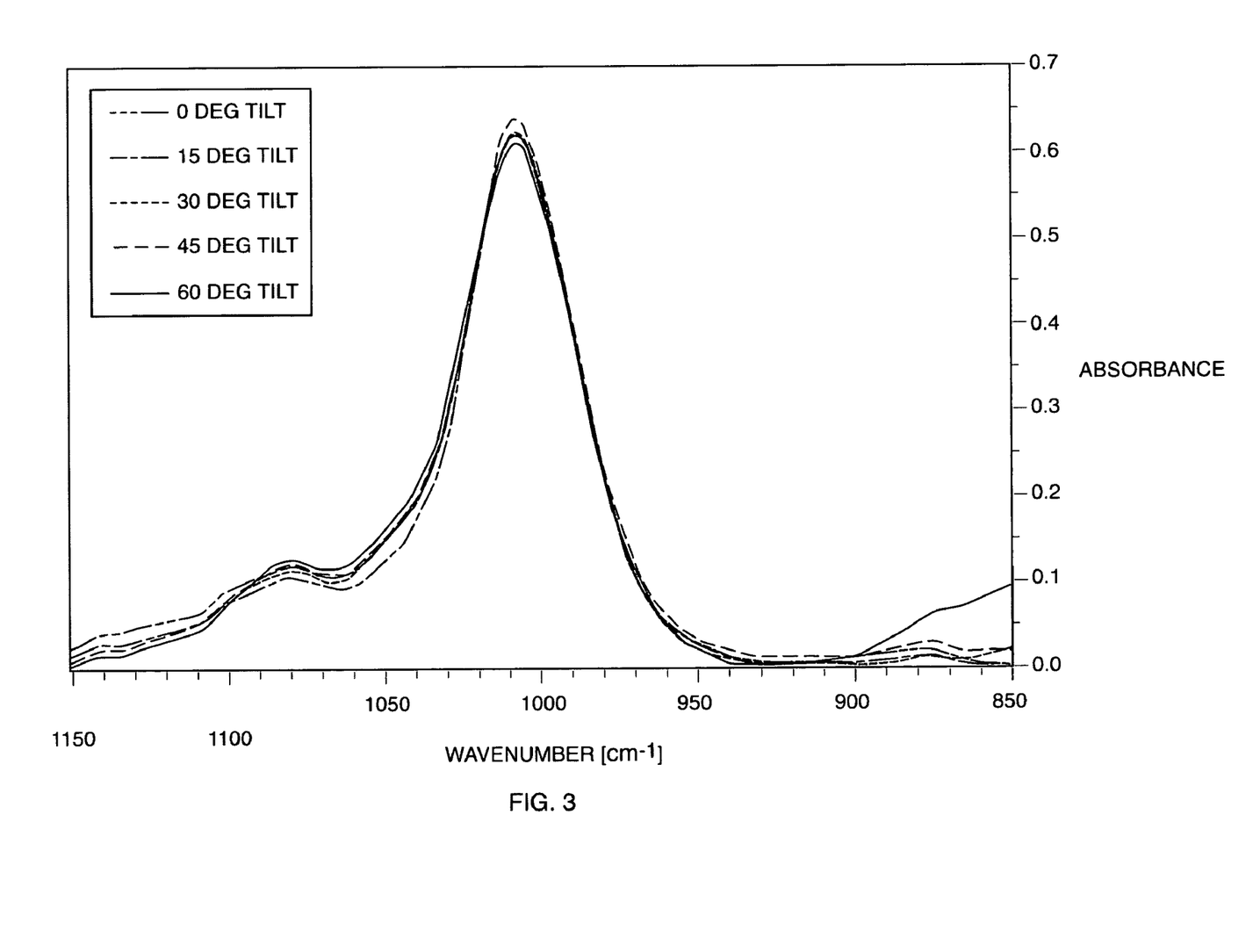
FIG. 3 shows differences in the infrared absorption as a function of tilt angle for organoclay polyethylene composites with light polarized in the y-direction.
Figure 4:
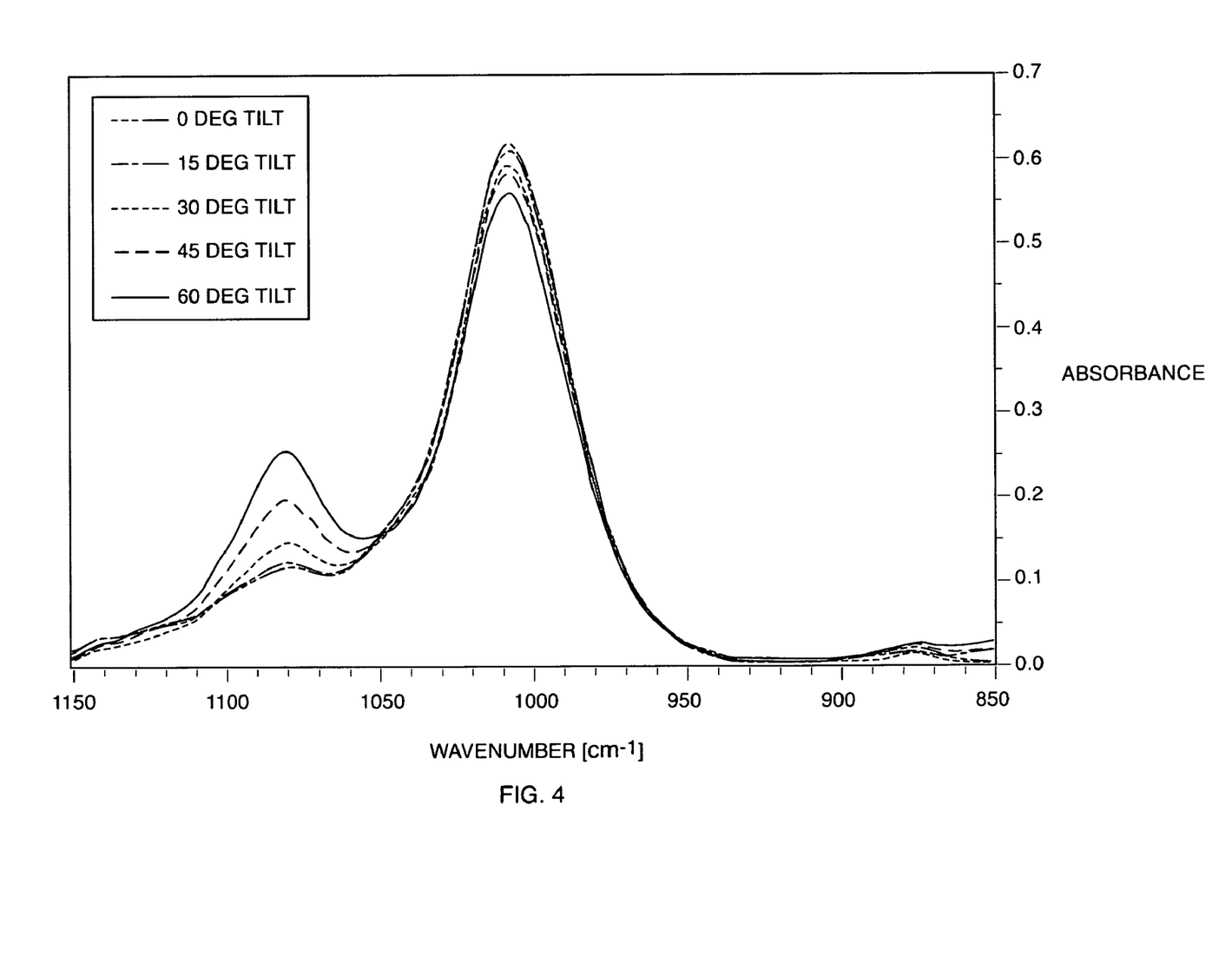
FIG. 4 shows differences in the infrared absorption as a function of tilt angle for organoclay polyethylene composites with light polarized in the z-direction.

Measuring the Degree of Layer Exfoliation of a BENTONE® 108-Polyethylene Nanocomposite and Collecting FTIR Spectra at Varying T z-Polarized Infrared Light About 5 wt % BENTONE® 108 organoclay was compounded into polyethylene using a twin screw extruder. A thin film of the resulting composite was prepared and the half width in-plane infrared absorption band was about 22 $cm^{-1}$ using unpolarized light, indicating that the composite contained about 65% exfoliated layers. XRD analysis showed that the remaining 35% organoclay was intercalated. Next, infrared absorption spectra were measured for this sample using light polarized along the y-axis and then the z-axis. The sample was tilted 0, 15, 30, 45 or 60 degrees around the y-axis. The absorption spectra for polarized light in the y- and z-axis directions are shown in FIGS. 3 and 4. Tilting of the sample while the light is polarized in the y-direction does not notably alter the infrared absorption as the sample orientation changes. However, when the light is polarized around the z-axis and the sample orientation is incrementally changed from 0 to 60 degrees, a decrease in absorption intensity is noted for the in-plane absorption band (around 1000 $cm^{-1}$), while an absorption increase is observed for the out-of-plane absorption band (around 1080 $cm^{-1}$). This absorption isotropy is ascribed to clay layer orientation within the polyethylene composite film. Note that the Si—O stretch bandwidth does not vary with the light polarization direction or with the sample orientation since the bandwidth only depends on the degree of clay nanodispersion and this does not change when tilting the sample.

Example 3

Figure 5:
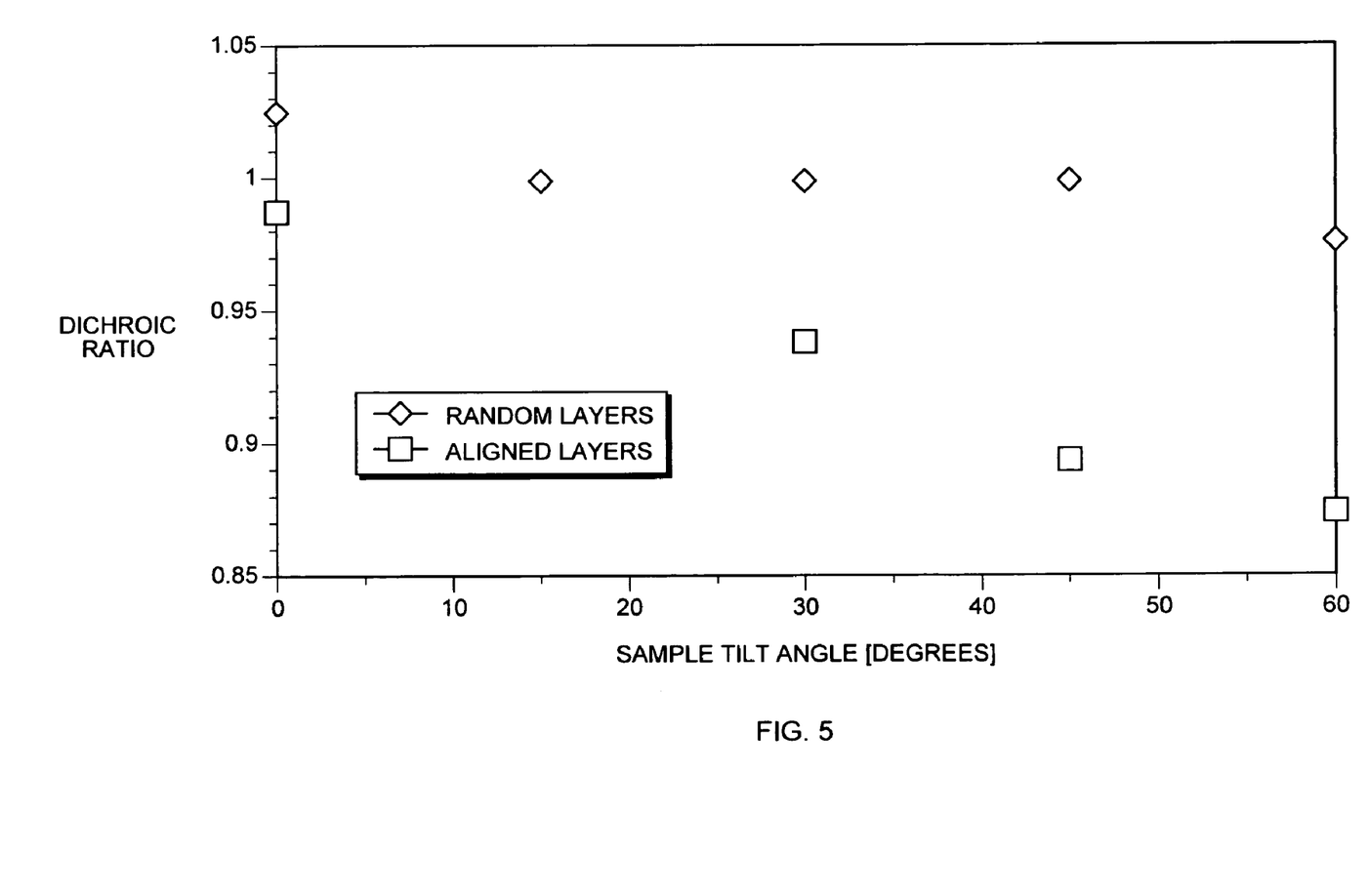
FIG. 5 shows dichroic ratios as a function of tilt angle for the in-plane Si—O absorption band.
Figure 6:
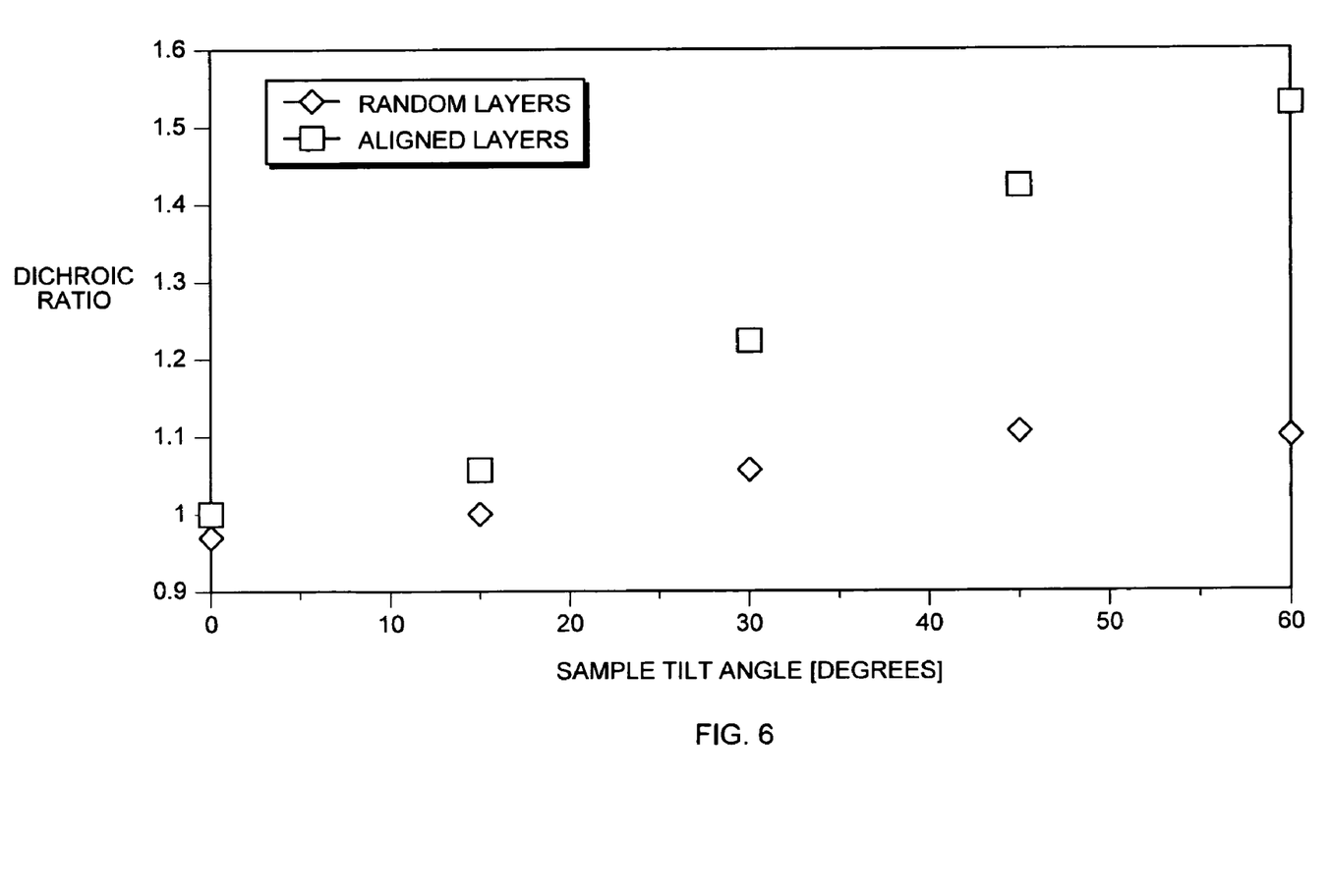
FIG. 6 shows dichroic ratios as a function of tilt angle for the out-of-plane Si—O absorption band.

Measuring the Layer Alignment (Orientation) in Organoclay Polymer Nanocomposites A 5 wt % BENTONE® 108—polyethylene exfoliated nanocomposite was prepared using the solvent cast method. A thin film was prepared to measure the infrared absorbance. The in-plane half width absorption band of this composite was about 18.5 $cm^{-1}$, indicating that virtually all organoclay was exfoliated. The clay layers are assumed to be aligned in this sample, as it is known that clay layers preferentially align themselves during film pressing. Part of the exfoliated composite was also used to prepare a second sample, but this composite was first ground to a fine powder and then mixed with KBr and pressed into a pellet. This pellet sample is assumed to have clay layers that are randomly oriented. The absorption spectra were recorded using polarized light while tilting the samples using the procedure as set forth in Example 2. The dichroic ratios were calculated from the intensities and plotted as a function of the sample tilting angle for both the 1000 $cm^{-1}$ and 1080 $cm^{-1}$ absorption bands, FIGS. 5 and 6 respectively. As expected, the dichroic ratio for the randomly oriented sample does not change much from unity when tilting the sample, particularly for the 1000 $cm^{-1}$ band. The 1080 $cm^{-1}$ absorption band does show some degree of orientation, as the dichroic ratio changes a little upon sample tilting. However, the changes in the dichroic ratio are far larger for the aligned clay layer sample, indicating that this sample has a higher degree of layer alignment. Dichroic ratios calculated from absorption band areas rather than absorption intensities show similar results. Above plots can be used to assess relative clay layer alignment differences between samples.

By using the method of this invention, it is possible to estimate the degree of clay exfoliation and clay layer alignment in a simple manner. These methods will allow the practitioner to tune his process parameters to obtain optimum results.

While certain embodiments of the invention have been illustrated, many alternative embodiments should become apparent to those skilled in this art without departing from the spirit and scope of the invention as set forth in the following claims.

What is claimed is:

1. A method for determining degree of clay or organoclay delamination and/or degree of layer alignment in a polymer clay or organoclay nanocomposite comprising one or more infrared light spectral measurements selected from the group consisting of (A) Si—O absorption bandwidth, (B) Si—O absorption band intensity, (C) Si—O absorption height, and (D) Si—O absorption anisotropy.

2. The method of claim 1 wherein the infrared light used is polarized.

3. The method of claim 1 wherein the nanocomposites comprise one or more polymers selected from the group consisting of polyethylene, polypropylene, polystyrene, polyester, EVA, polyamides, urea-formaldehydes, and melamine-formaldehydes.

4. The method of claim 1 wherein the absorption anisotropy is derived from a dichroic ratios obtained from the in-plane or out-of-plane Si—O clay bonds from a plurality of composite tilt angles.

5. The method of claim 1 wherein the clay or clay component of the organoclay is one or more smectite clays.

6. The method of claim 5 wherein the clay or clay component of the organoclay is a smectite clay selected from the group consisting of: montmorillonite, particularly sodium montmorillonite; bentonite; hectorite; saponite; stevensite; and beidellite.

7. The method of claim 6 wherein the clay or clay component of the organoclay is a smectite clay is selected from the group consisting of bentonite and hectorite.

8. The method of claim 5 wherein the nanocomposite is comprised of polyolefin polymer and an organoclay containing a hectorite clay component.

9. The method of claim 1 wherein the spectral measurements of the Si—O absorption are calculated by subtracting the polymer spectra from the composite spectra.

* * * * *